(12) United States Patent
Gattani et al.

(10) Patent No.: US 8,116,847 B2
(45) Date of Patent: Feb. 14, 2012

(54) SYSTEM AND METHOD FOR DETERMINING AN OPTIMAL SURGICAL TRAJECTORY

(75) Inventors: Abhishek Gattani, San Jose, CA (US); Salmaan Hameed, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 1394 days.

(21) Appl. No.: 11/583,295

(22) Filed: Oct. 19, 2006

(65) Prior Publication Data

US 2008/0097165 A1    Apr. 24, 2008

(51) Int. Cl.
*A61B 8/00* (2006.01)

(52) U.S. Cl. ............. 600/424; 382/131; 382/132; 378/4

(58) Field of Classification Search ................. 600/300, 600/424; 382/128, 131–132; 378/4
See application file for complete search history.

(56) References Cited

U.S. PATENT DOCUMENTS

| | | | |
|---|---|---|---|
| 6,191,796 B1 * | 2/2001 | Tarr | 345/581 |
| 6,390,097 B1 * | 5/2002 | Chandra | 128/898 |
| 6,833,814 B2 * | 12/2004 | Gilboa et al. | 342/448 |
| 7,397,886 B2 * | 7/2008 | Avinash et al. | 378/5 |
| 2005/0101970 A1 * | 5/2005 | Rosenberg | 606/130 |
| 2005/0119559 A1 * | 6/2005 | Van Vaals et al. | 600/425 |
| 2006/0189842 A1 * | 8/2006 | Hoeg et al. | 600/118 |
| 2008/0020362 A1 * | 1/2008 | Cotin et al. | 434/267 |
| 2008/0097293 A1 * | 4/2008 | Chin et al. | 604/95.04 |

* cited by examiner

*Primary Examiner* — Brian Casler
*Assistant Examiner* — Daniel Huntley
(74) *Attorney, Agent, or Firm* — Flynn, Thiel, Boutell & Tanis, P.C.

(57) ABSTRACT

A method and corresponding system for calculating an optimum surgical trajectory or path for displacing a surgical instrument through the interior of the body of a patient. Upon obtaining a volumetric scan of a patient, such as a CT scan, the surgeon can identify and assign weight values indicating a preference on whether an anatomical area be utilized in plotting an optimum instrument trajectory. Upon providing a starting and destination point for a surgical instrument, an optimum surgical trajectory can be determined in essentially real time and graphically presented to the surgeon by superimposing the proposed trajectory upon the patient's volumetric scan. Furthermore, the system and method is interactive, allowing the surgeon to deviate from the proposed optimum path if desired and choose another path. In response, the system will determine and present, in essentially real time, a new optimum trajectory based on the current location of the surgical instrument.

51 Claims, 14 Drawing Sheets

|  | V1 | V2 | V3 | V4 | V5 |
| --- | --- | --- | --- | --- | --- |
| V1 | ∞ | P | ∞ | P | P |
| V2 | ∞ | ∞ | ∞ | P | ∞ |
| V3 | ∞ | ∞ | ∞ | ∞ | P |
| V4 | ∞ | ∞ | ∞ | ∞ | ∞ |
| V5 | ∞ | P | ∞ | ∞ | ∞ |

Modifed Version of Floyd's Algorithm

```
    CVFloyd (int N, rmatrix &C, rmatrix &D,
imatrix &P)
    {
      int i,j,k;
      for (i = 0; i < N; i++) {
        for (j = 0; j < N; j++) {
           D[i][j] = C[i][j];
           P[i][j] = -1;
        }
        D[i][i] = 0.0;
      }
      for (k = 0; k < N; k++) {
        for (i = 0; i < N; i++) {
          for (j = 0; j < N; j++) {
            if (D[i][k] + D[k][j] < D[i][j] and
|A[i][K].A[k][j]|<|cos(alpha)| {
                D[i][j] = D[i][k] + D[k][j];
                P[i][j] = k;
      } } } }
    }
```

Fig. 14

SYSTEM AND METHOD FOR DETERMINING AN OPTIMAL SURGICAL TRAJECTORY

FIELD OF THE INVENTION

The present invention relates to a system and method for determining an optimal trajectory or path for a surgical instrument being displaced within the body of a patient, as well as a system and method for presenting to a surgeon, in real time, an optimal surgical trajectory for navigating an instrument during a surgical procedure.

BACKGROUND OF THE INVENTION

A primary goal of minimally invasive surgical procedures is to minimize the adverse effects of the procedure on the patient. This reduces post-surgical trauma and pain and minimizes recovery time. Some minimally invasive procedures require the surgeon to create one or more small incisions through which various surgical instruments can be passed. Other minimally invasive procedures forego the need to create small incisions in the exterior of the patient, instead relying on surgical instruments such as, for example, flexible endoscopes that can be passed into the interior of the patient's body by entry through a natural bodily orifice.

FIGS. 1 and 2 depict a traditional flexible endoscope 20 which can be utilized by a surgeon to remotely view and manipulate tissue within the body of a patient. As illustrated in FIG. 1, a traditional flexible endoscope 20 generally comprises a control body 22 that connects to an insertion tube 24. The control body 22 remains outside the patient, while the flexible insertion tube 24 is inserted into the interior of the patient via either a naturally occurring or man-made orifice. Depending on the intended function of a specific flexible endoscope, the insertion tube 24 can include, for example, various channels for performing suction, biopsy, irrigation and insufflation. The insertion tube 24 may also include fiber optics or light bundles for conveying light from an external light source to the interior of the patient, as well as conveying images from the interior to an exterior camera. A connector 32 allows the endoscope 20 to connect to one or more various related system components, including, for example, a power supply, a light source, a camera and/or video processor. Endoscope 20 may also include additional control means 30 for controlling one or more functions of the endoscope, such as, for example, a manipulator or other tissue processing means that extends out from the distal tip section 26 of the endoscope 20.

In practice, the insertion tube 24 is inserted into a man-made or naturally occurring orifice of the patient and then slowly advanced into the interior of the patient. One or more controls 28 typically located on the body 22 of the endoscope 20 allows for the surgeon to manipulate or bend the distal tip section 26 of the flexible endoscope as he or she advances the insertion tube 24 through the patient. In this manner, the surgeon can steer the tip 26 of the endoscope as it is advanced through the interior of the patient's body.

Thus, as illustrated in the example of FIG. 2, a surgeon can utilize a flexible endoscope 20 to view and manipulate the tissue of a patient's upper gastrointestinal tract, and beyond, by inserting the distal tip section 26 of the endoscope 20 into the mouth 44 of the patient 42. The surgeon then advances the insertion tube 24 down the patient's esophagus 46 until the tip region 26 of the endoscope 20 is in the region of tissue that he or she wishes to examine, i.e., the stomach 48 or duodenum 50. Alternatively, if the region of tissue that the surgeon wishes to examine lies beyond the stomach 48, the surgeon can utilize the flexible endoscope 20 or other surgical instrument to make an incision in the wall of the stomach 48. The flexible endoscope 20 can then be passed through the newly-created incision and advanced outside the stomach 48, allowing the surgeon to examine the exterior of the stomach 48 and surrounding tissue, or alternatively, advance the endoscope 20 beyond the surrounding tissue in order to examine anatomical regions more distant from the stomach 48.

As demonstrated by the above example, endoscopic surgical procedures typically involve the surgeon having to examine and work upon a target area of tissue that is located some distance from the opening (e.g., naturally occurring or man-made orifice) that the surgical instrument is passed through in order to gain entry into the interior of the patient body. Furthermore, as the distance between the opening and target area of tissue increases, so does the complexity of the surgical procedure. Guiding the endoscope through the tissue of the patient to the target area may be relatively straightforward when the target area of tissue is located adjacent or proximal to the opening through which the endoscope enters the interior of the patient. However, as the distance between the opening and target area of tissue increases, so does the complexity of the endoscopic procedure. An increasing distance between the opening and target area of tissue results in the potential number of paths that the endoscope can be guided along to increase exponentially.

When presented with numerous potential surgical trajectories or paths between the opening and target area of tissue, the surgeon is then faced with the problem of determining and following the one trajectory that is deemed most optimal for the surgical procedure. Usually the most optimal trajectory is considered to be the path that minimizes the potential for tissue damage to the patient while still delivering the endoscope to the target area. In current endoscopic procedures, determination of the optimal surgical trajectory is made solely by the surgeon based on his or her anatomical knowledge and prior surgical experience. Consequently, a procedure performed by a seasoned, highly-experienced surgeon may result in the selection of the most optimal and safest surgical trajectory, while the same procedure performed by a younger, less-experienced surgeon may result in the selection of a less-than-optimal surgical trajectory that can increase the chance of complications during the procedure.

Disadvantages in current navigational methods continue to exist even when only highly-skilled surgeons are performing the procedures. Variations among surgeons with respect to procedural methods and preferences can result in significant differences in the selection of the optimal surgical trajectory for a specific surgical procedure. The selection of a sub-optimal trajectory by even the most skilled surgeon can also occur simply due to time constraints. The typical surgical schedule can be quite hectic, providing the surgeon with limited time to spend on analyzing and planning an upcoming surgery. Consequently, the surgeon may not have considered the selection of many different, or possibly any, alternative trajectories or paths. Determining and selecting the optimal surgical trajectory becomes even more difficult during the surgical procedure itself. Even if an initial optimal trajectory was selected during the beginning of the procedure, many surgeons end up having to revise their earlier decision and select a new trajectory as the procedure progresses due to factors such as anatomical variation amongst patients as well as virtually any minor or major surgical complication that results in the surgeon having to deviate from their initial plan.

SUMMARY OF THE INVENTION

The present invention, according to a first embodiment, is a method of determining an optimum trajectory for displacing a surgical instrument through the interior of a body of a patient. Weight values, indicating a degree of preference that a specified region be utilized as part of the optimum trajectory, are assigned to one or more regions of a volumetric scan of the patient. The optimum surgical trajectory between every two non-adjacent regions within the volumetric scan is then calculated. An optimum surgical trajectory is then presented to a user in response to the identification of a starting region and destination region within the volumetric scan. In response to changes in the current position of the surgical instrument, the optimum surgical trajectory is revised in essentially real time.

According to another embodiment, the invention comprises a method of aiding a surgeon in guiding a surgical instrument through the body of the patient. After a volumetric scan of the body is obtained, an initial optimum path for displacing the surgical instrument from its current position to a designated destination position is determined and presented to the surgeon. When displacement of the surgical instrument has been detected during the surgical procedure, a new optimum path is determined and presented to the surgeon in essentially real time.

In an alternative embodiment, the method of aiding a surgeon in guiding a surgical instrument through the body of the patient includes the step of calculating a trajectory for displacing the surgical instrument between any position in the scan to any other position in the scan. A current position of the surgical instrument is detected during the surgical procedure. Then the surgeon is presented, in real-time, the optimum path for displacing the surgical instrument from its currently detected position to a designated destination position. In response to displacement of the surgical instrument, the optimum path presented to the surgeon is revised in real time.

In yet another embodiment, the present invention comprises a system for aiding a surgeon in guiding a surgical instrument through the body of a patient. Included in the system is a central controller having at least one data input means as well as computational means, an electromagnetic tracking system for determining the position and orientation of the surgical instrument, and at least one monitor for displaying a volumetric scan of the patient and/or images captured by the surgical instrument.

BRIEF DESCRIPTION OF THE DRAWINGS

One or more embodiments of the present invention are illustrated by way of example and should not be construed as being limited to the specific embodiments depicted in the accompanying drawings, in which like references indicate similar elements and in which:

FIG. 14 depicts a modified version of Floyd's algorithm according to one embodiment of the invention.

DETAILED DESCRIPTION

Figure 1:
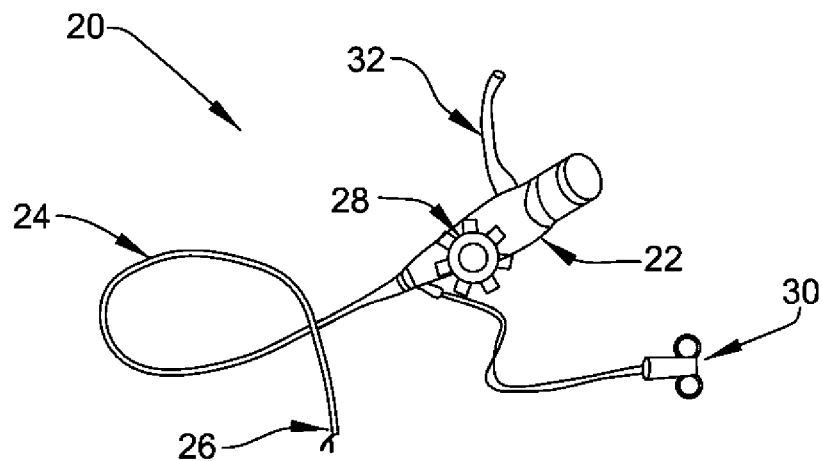
FIG. 1 illustrates a traditional flexible endoscope.
Figure 2:
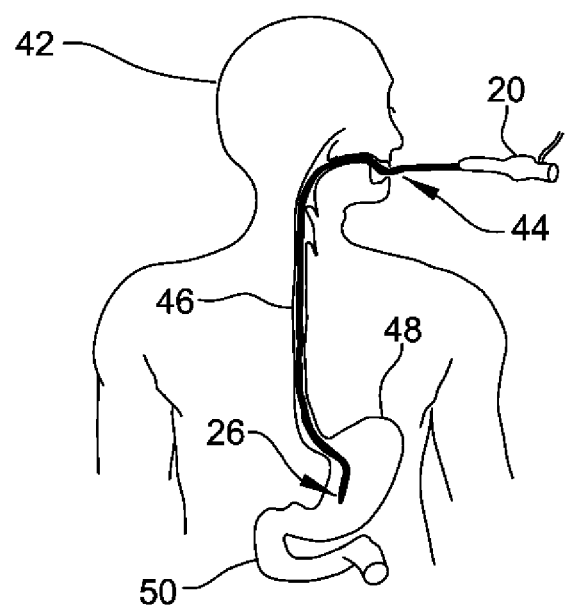
FIG. 2 illustrates the use of a flexible endoscope to examine and/or manipulate the tissue of a patient's upper gastrointestinal tract.
Figure 3:
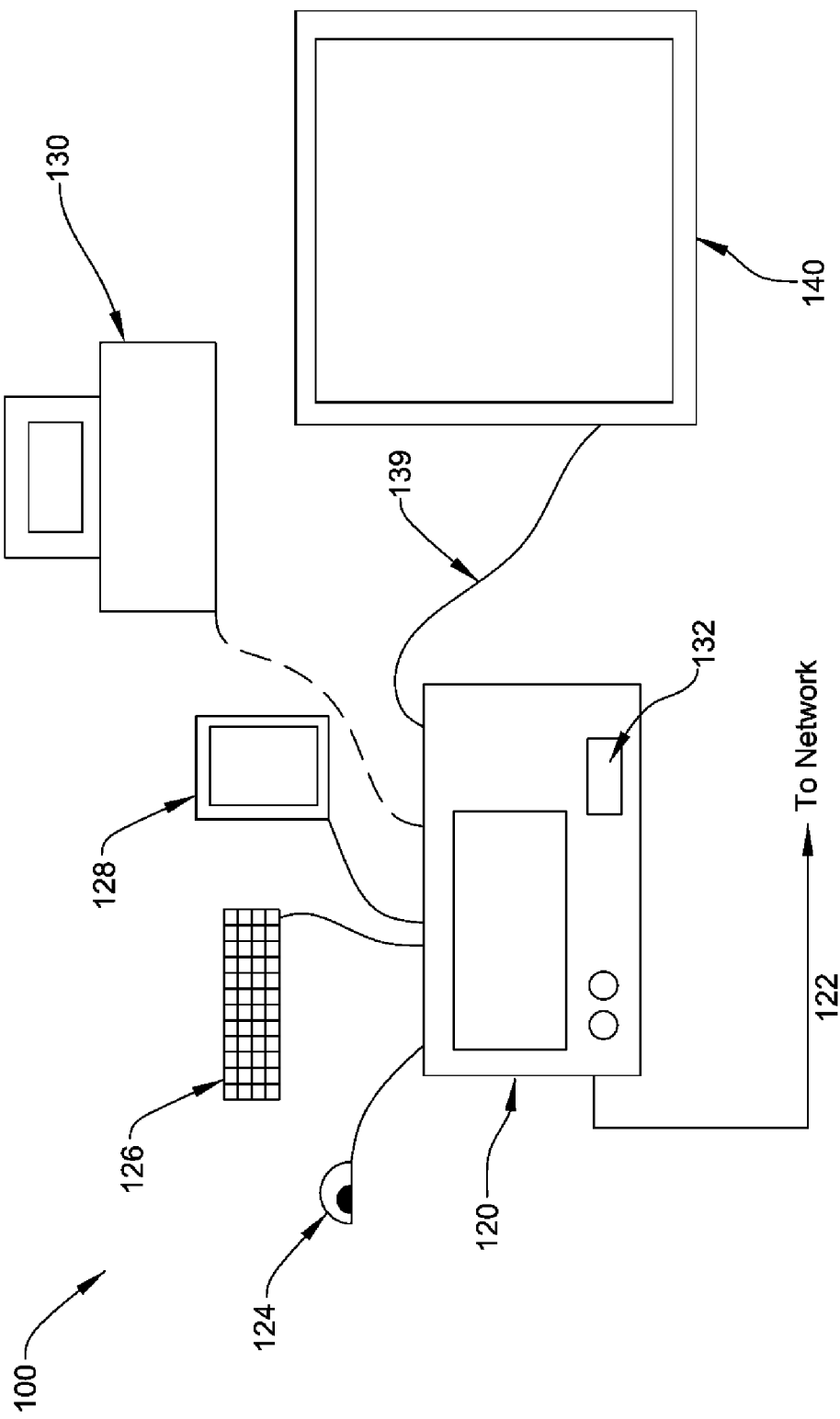
FIG. 3 illustrates a system for computing an optimal trajectory or path for a surgical instrument being displaced within the body of a patient.

FIG. 3 depicts a system 100 for calculating in real time an optimal surgical trajectory or path for displacing a surgical instrument through the interior of the patient body. If a first determined optimal surgical trajectory is either deviated from or rejected, the system is able to determine and present a new optimal trajectory in essentially real time.

According to the present embodiment, the surgical trajectory determination system 100 includes a central controller 120 configured to receive various information, calculate an optimal surgical trajectory, and present a calculated trajectory to a user. Received information can relate to various factors, including, for example, surgical preferences, instrument parameters, and patient data.

Connecting to central controller 120 can be one or more human interface devices, such as, for example, a mouse 124, keyboard 126 and graphics tablet 128, which can be utilized by the surgeon or other users to input patient and surgical data into, and retrieve data from, the central controller 120. One or more separate computers 130 may be configured to interface with central controller 120 as an alternative, or in addition to, the human interface devices 124-128. To facilitate the exchange of data, such as patient images and records, with other surgical or hospital systems, central controller 120 may include a network interface adapter 122. Central controller 120 may also include one or more interfaces 132 capable of receiving removable media such as, for example, a USB flash memory drive or compact flash card.

Also connecting to the central controller 120 via either an associated wire connection 139 or wirelessly is at least one display monitor 140 configured to display various information to the surgeon. Such displayed information can include, but is not limited to, endoscopic images of the patient body acquired by a surgical instrument, previously acquired patient scans such as CT scans, X-rays, PET scans, MRI scans and the like, as well as various information generated by the central controller 120 to facilitate the selection and following of an optimal surgical trajectory or endoscopic path.

The present invention can be configured to calculate and present optimal surgical trajectories for a variety of surgical instruments, including but not limited to a catheter, a guide wire, a pointer probe, a stent, an implant, and various forms of endoscopes (including a rigid endoscope, semi-rigid endoscope, or flexible endoscope). For purposes of example, the remainder of the discussion will frequently make reference to the surgical instrument as being a flexible endoscope. However, it should be kept in mind that the present invention can be utilized with virtually any surgical instrument that is designed to be inserted into and displaced through the interior of a patient body.

Acquiring a Volumetric Scan of the Patient

Figure 4:
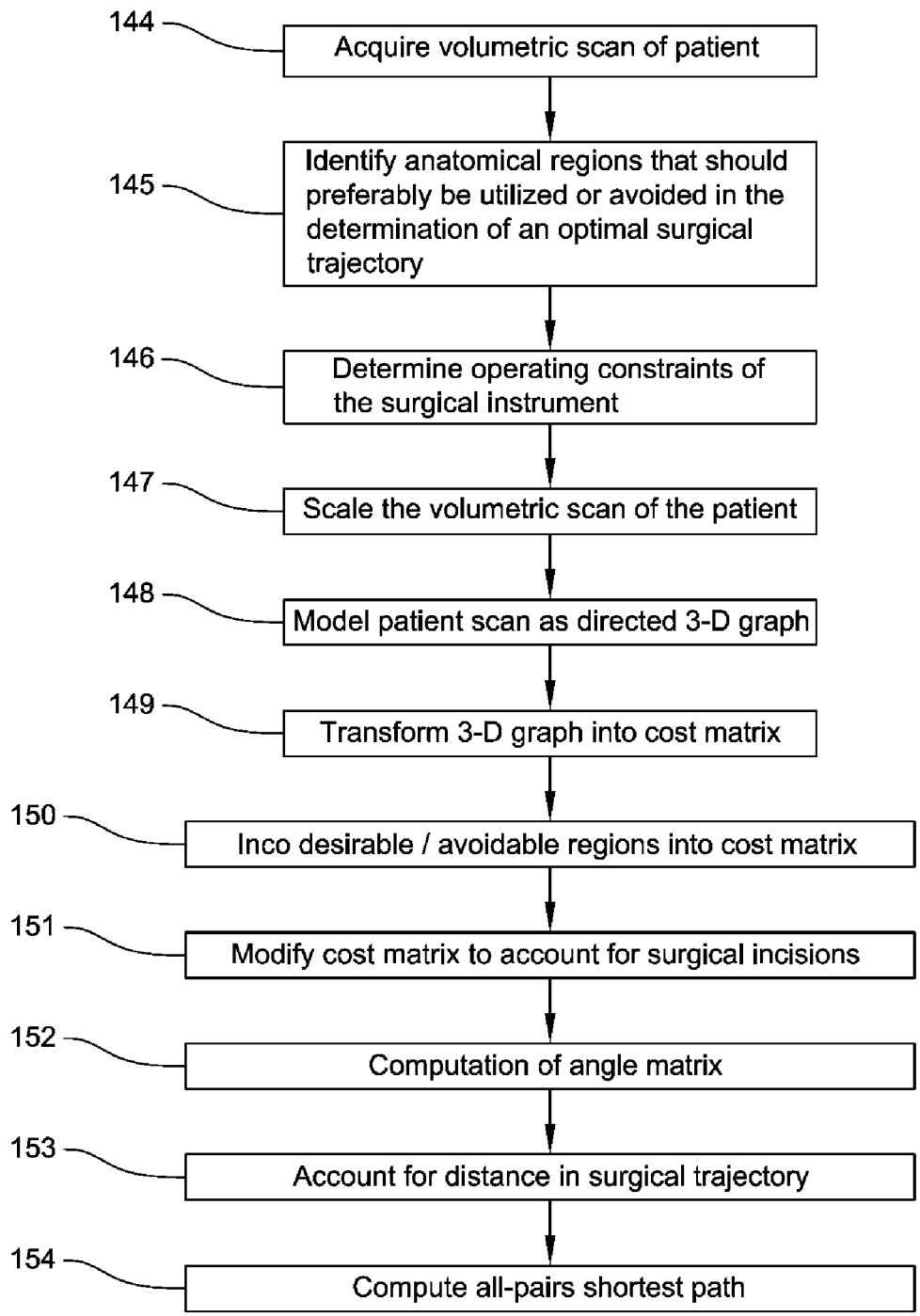
FIG. 4 is a flow chart depicting the general steps involved in determining an optimum surgical trajectory according to one embodiment.

The basic operation of surgical navigation system 100, as described above, will now be discussed with reference to the embodiment illustrated in the flow chart of FIG. 4. Prior to the surgical procedure, one or more images or scans of the patient are first acquired (Step 144). According to the current embodiment, the acquired images of the patient are computed tomography (CT) or computerized axial tomography (CAT) scans (hereafter simply referred to as CT scans) that measure the radiodensity of tissue. However, the present invention is not limited to CT scans, but can be applied with various other volumetric scanning modalities capable of measuring and mapping tissue. Some of these additional modalities include, for example, x-ray images that also measure the radiodensity of tissue, positron emission tomography (PET) scans that measure the emittance of radiotracers introduced into the body, magnetic resonance imaging (MRI) scans that measure the anatomical magnetic resonance of tissue, and ultrasound scans that measure the anatomical acoustic reflectivity of tissue. For purposes of example for the remainder of the disclosure, all reference to patient images or scans will be understood to mean CT scans.

Figure 5:
FIG. 5 is an example illustration of a CT/CAT scan.

FIG. 5 depicts a slice of a sample computed tomography (CT) scan of a patient's upper shoulder region and lower head that was produced by passing multiple x-rays through the body of the patient. The resultant image indicates the relative radiodensity, or transparency to the passage of x-rays, of the various tissues. Typically in CT scans, dense tissue such as bone 160 will appear white, less dense tissue such as fat and muscle 162 will appear as various shades of gray, and dilute or non-dense substances such as air 164 trapped in a person's larynx or windpipe will appear black.

Quantification of Radiodensity and Hounsfield Units

Fundamental to many CT scanning applications is the quantification of a substance's radiodensity according to the Hounsfield scale. Reference substances within the Hounsfield scale include distilled water, which is assigned a value of 0 units, and air, which is specified as −1000 units. Other substances and their corresponding Hounsfield values are provided below in Table 1.

TABLE 1

HU Values of Common Substances

| Substance | Hounsfield units (HU) |
|---|---|
| Air | −1000 |
| Fat | −120 |
| Water | 0 |
| Muscle | +40 |
| Bone | +1000 |

By utilizing the Hounsfield scale, the CT scan is reconfigured into a detailed radiodensity map of the human body. For illustrative purposes, consider the two-dimensional slice of a three-dimensional CT scan of FIG. 5. For purposes of example, the depicted slice will be considered as being equivalent to a two-dimensional x-ray. As a result, if FIG. 5 was sufficiently magnified, it would be seen as comprising a plurality of picture elements or "pixels", which are the smallest distinguishable unit of area within the image. Furthermore, each such pixel, being a unique unit of area within the scan of FIG. 5, is associated with a specific radiodensity or Hounsfield unit (HU) value.

Figure 6:
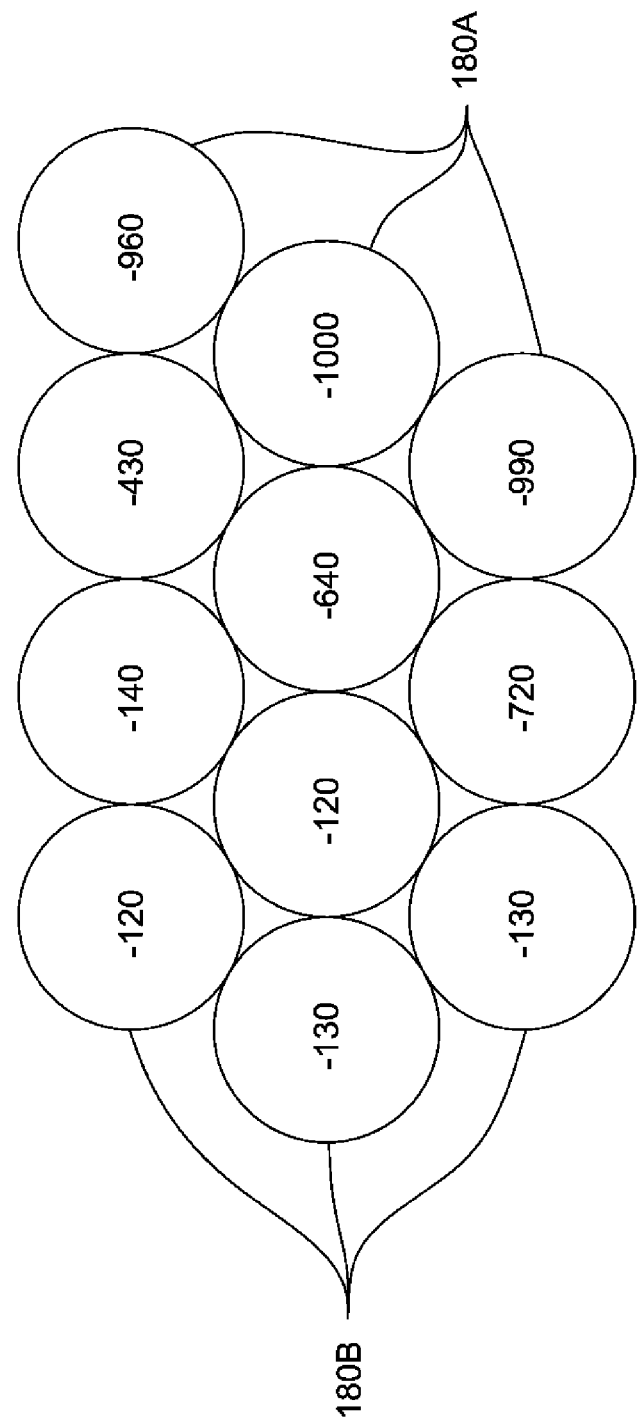
FIG. 6 is a magnified view of a two-dimensional CT/CAT scan depicting the individual pixels making up the image.

FIG. 6 is an example representation of what would be seen if an area of the two-dimensional scan of the example above were sufficiently magnified to depict the individual pixels of the image. Each such pixel 180, representing the smallest distinguishable unit of area within the scan, has an associated HU value representing the radiodensity of that specific area. As illustrated in the example of FIG. 6, the pixels 180A along the right side of the figure are seen to have extremely low HU values, indicating that these pixels likely represent an area of air (HU of −1000). In contrast, the pixels 180B along the left side of FIG. 6 have significantly higher HU values, possibly indicating that these pixels represent an area of fatty tissue (HU of −120).

2-D Pixels vs. 3-D Voxels

Due to obvious limitations in how the disclosure of the current application can be presented, FIG. 5 is limited to depicting a two-dimensional representation of a CT scan. However, in real life, computerized tomography (CT) systems are configured to generate three-dimensional representations of the patient body and its corresponding radiodensities. Upon sufficient magnification, such a three-dimensional representation or scan is seen as not being comprised of a plurality of pixels, but instead comprised of a plurality of "voxels", the smallest distinguishable unit of volume and three-dimensional equivalent of a pixel.

In a manner similar to pixels, each voxel that makes up part of a three-dimensional CT scan represents the smallest distinguishable unit of volume within that scan. Furthermore, just like pixels, each such voxel or unit of volume of a three-dimensional CT scan is associated with a specific radiodensity or Hounsfield unit (HU) value.

Figure 7:
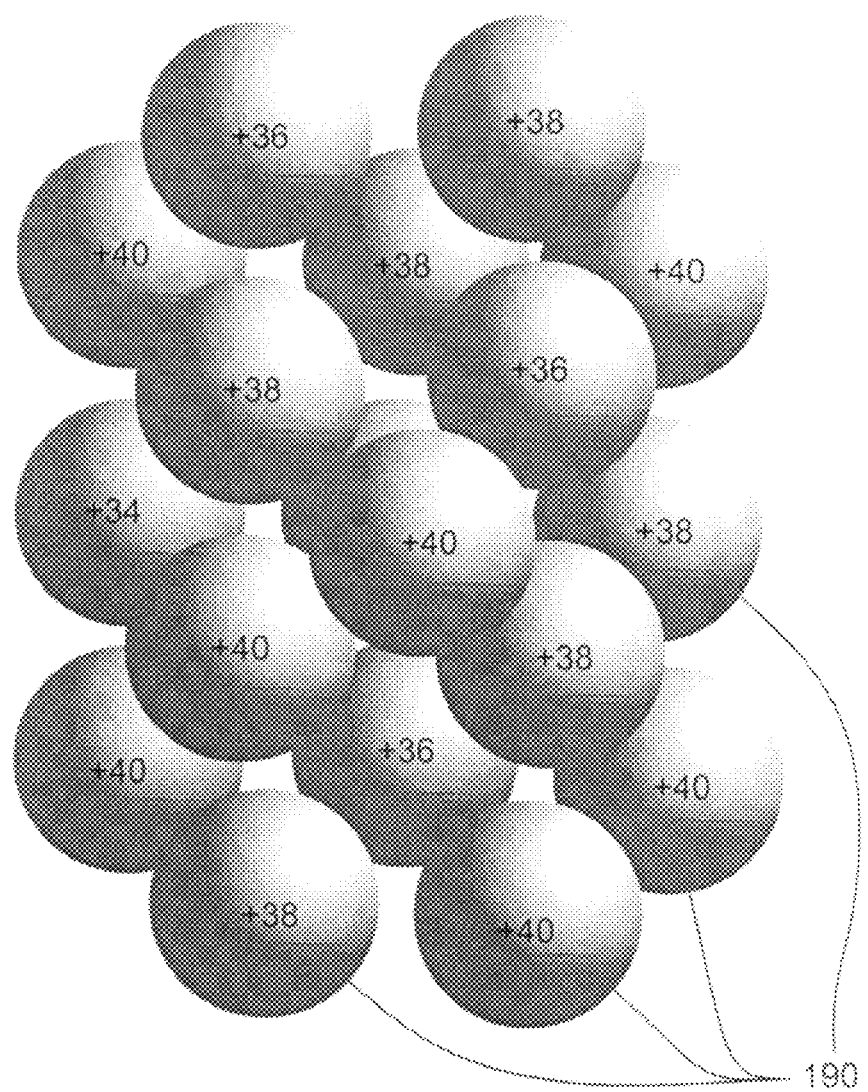
FIG. 7 is a magnified view of a specified volume of a three-dimensional CT/CAT scan depicting the individual voxels making up the image.

FIG. 7 is an example representation of what would be seen if a specified volume of a three-dimensional CT scan were sufficiently magnified to depict the individual voxels of the three-dimensional image. Each such voxel 190, representing the smallest distinguishable unit of volume within the CT scan, has a corresponding HU value representing the radiodensity of that specific volume. As illustrated in the example of FIG. 7, voxels 190 have radiodensity values around +40 Hounsfield units, indicating that the volume of tissue corresponding to this area of the CT scan is likely comprised of muscle tissue.

Identifying Anatomical Regions that should be Preferred or Avoided in the Determination of an Optimal Surgical Trajectory Prior to initiation of the surgical procedure, the surgeon can program the surgical navigation system 100 to indicate those anatomical areas that should preferably be avoided during the surgical procedure (Step 145). Anatomical areas to avoid generally comprise, for example, regions of tissue that are highly vulnerable to damage, such as arteries or veins, or areas that are simply too risky to pass through, such as critical organs.

Similarly, the surgeon can program the system 100 to indicate those anatomical areas that facilitate the routing of a surgical instrument and thus are highly desirable to utilize as part of an optimum surgical trajectory (Step 145). Such anatomical areas that facilitate the routing of a surgical instrument include, for example, tubular organs and hollow or low density tissue such as the esophagus, stomach, colon and sinus cavities.

According to one embodiment, a surgeon can program the surgical navigation system 100 by means of a template file that contains a map indicating those anatomical regions within the human body that are desirable to use as part of a surgical trajectory, as well as those anatomical regions that should be avoided during the surgical procedure. A template file can be customized in varying degrees and for numerous circumstances, including specific surgical procedures, specific surgeons, and even specific medical conditions.

According to another embodiment, the template files are stored on the central controller 120 and can be retrieved and implemented at the central controller 120 by a surgeon prior to initiation of a surgical procedure. Alternatively, the template files can be stored on and retrieved from a remote server via the network interface 122. In yet another embodiment, the one or more template files can be stored on removable media, such as compact disc, flash memory and the like, which can be loaded onto the central controller 120 by means of interface 132.

According to one embodiment, a template is mathematically defined as a real-valued weight function t: H→W, where H is the Hounsfield radiodensity value and W is a weight value assigned to that particular Hounsfield value. Based on the weight values W associated with the Hounsfield values H, each voxel, representing the smallest distinguishable unit of volume in a patient's CT scan, is assigned a specific weight value W. A mapping m is then produced based on the function m: X→W, where X is a point (voxel) in the patient's CT scan and W is the weight value assigned to that point.

The weight values W assigned to each point in a patient's CT scan will subsequently be utilized by the system 100 to determine the amount of preference each point should be given when calculating an optimum surgical trajectory or path that the surgeon should follow when guiding a surgical instrument through the patient body. According to one embodiment, the weight values W are adjusted Hounsfield radiodensity values. Alternatively, the weight values W are defined by a predetermined discretionary scale, with values at one end of the scale indicating a strong preference that an anatomical area be utilized when calculating an optimum surgical trajectory, while values at the other end of the scale indicating a strong preference that an anatomical area be avoided when calculating the surgical trajectory.

According to another embodiment, the surgeon can also program the system 100 to indicate the anatomical areas that he or she wishes to avoid or preferably utilize in the development of an optimum surgical trajectory by manually identifying regions on the patient's CT scan and then associating those identified regions with particular weight values W. As demonstrated in FIG. 8, the surgeon creates this second form of template by manually marking up regions 202 on the patient's CT scan 200 by means of one or more human interface devices as previously identified. The surgeon then assigns weight values to the selected regions 202 indicating the surgeon's degree of preference on whether the system 100 utilizes or avoids the selected anatomical regions in calculating an optimum surgical trajectory or path.

Figure 8:
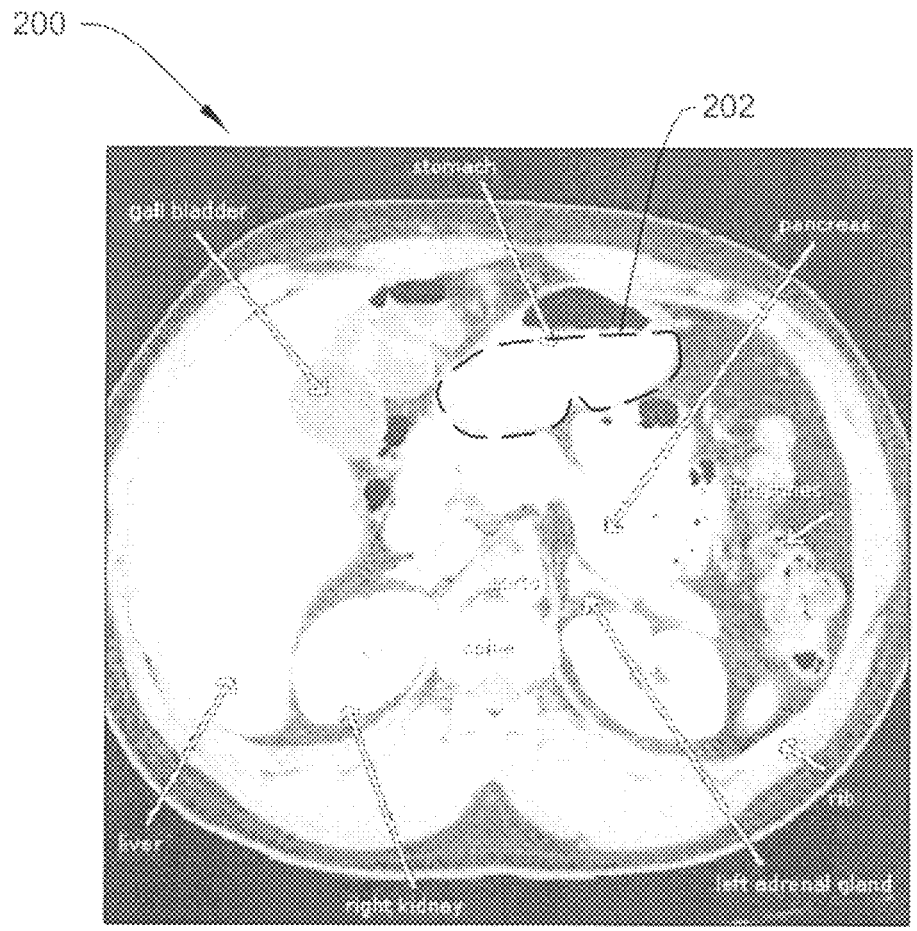
FIG. 8 is an example illustration of a CT/CAT scan marked up by a surgeon to indicate an anatomical region that should be preferably utilized in calculating an optimum surgical trajectory.

Similar to the previous embodiment, the system 100 then produces a map m based on the function m: X→W, where X is a point (e.g., voxel) in the patient's CT scan and W is the weight value that the surgeon assigned to that area of the scan that the point X resides within. In the example of FIG. 8, a slice of a patient's CT scan 200, depicting the abdominal area of the patient, has been marked up to identify the stomach. The surgeon can then, for example, assign a weight value to the stomach indicating that this anatomical area should be given significant preference by the system 100 when the system 100 determines what anatomical areas should be utilized in the development of an optimum surgical trajectory.

Either type of map m identified in the embodiments above can be utilized individually or in combination to program the surgical navigation system 100 to indicate those anatomical areas that should preferably be utilized or avoided during the surgical procedure.

Determining the Operative Constraints of a Surgical Instrument

In determining an optimum surgical path, the navigational system 100 can also account for any operative constraints of the surgical instrument or instruments that are to be used during a specific surgical procedure (Step 146). One example of an instrument operating constraint is the physical dimensions of the smallest rigid segment of that portion of the instrument that is to be inserted and guided through the patient's body. Another example of an instrument operating constraint that can be taken into account in determining an optimum surgical path is the smallest volume and/or unit of length that the instrument can be displaced when guided through the patient's body. If instrument operating constraints such as those described above are not taken into account in the determination of an optimum surgical trajectory, the navigational system 100 may propose an optimum trajectory or path to the surgeon that is otherwise difficult and/or impossible for the surgeon to guide the surgical instrument along during the procedure.

Figure 9:
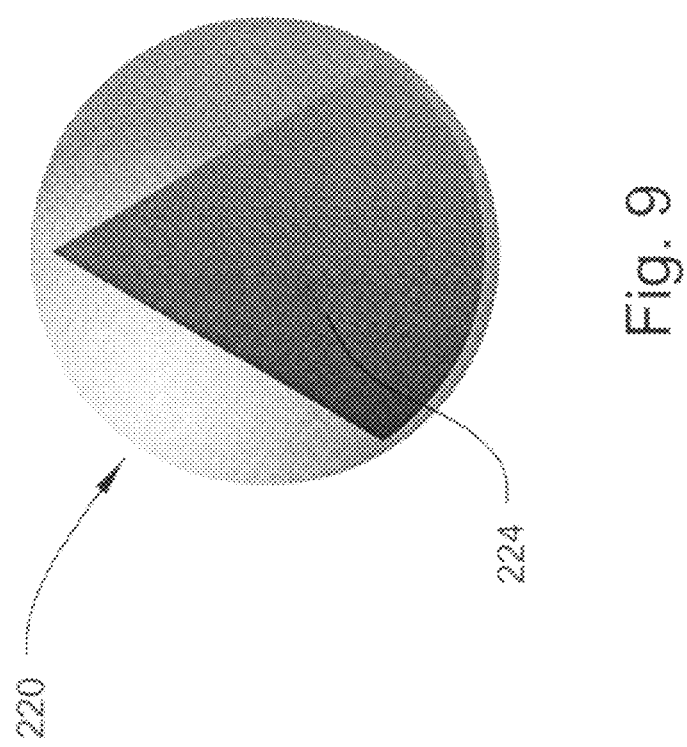
FIG. 9 illustrates a bounding sphere encompassing a sample object.

In one embodiment, an instrument operating constraint, such as the dimensions of the smallest rigid segment of the instrument and its center of rotation, is computed by means of a bounding sphere. As illustrated in FIG. 9, a bounding sphere 220 is a hypothetical sphere that completely encompasses an object 224 or set of objects based on the object or objects movement about their center of rotation.

In mathematics, given a non-empty set of objects of finite extension in n-dimensional space, for example, a set of points, a bounding sphere for that set of points is an n-dimensional solid sphere containing each of these objects. The bounding sphere is defined by a three-dimensional coordinate representing the center and scalar radius of the sphere. When defining a bounding sphere, one typically tries to find the minimal sphere size that provides the tightest fit for the bounded object or objects, thereby producing the smallest radius sphere within which lie all operational points. The object is subsequently rotated about its center and a point cloud is obtained.

Figure 10:
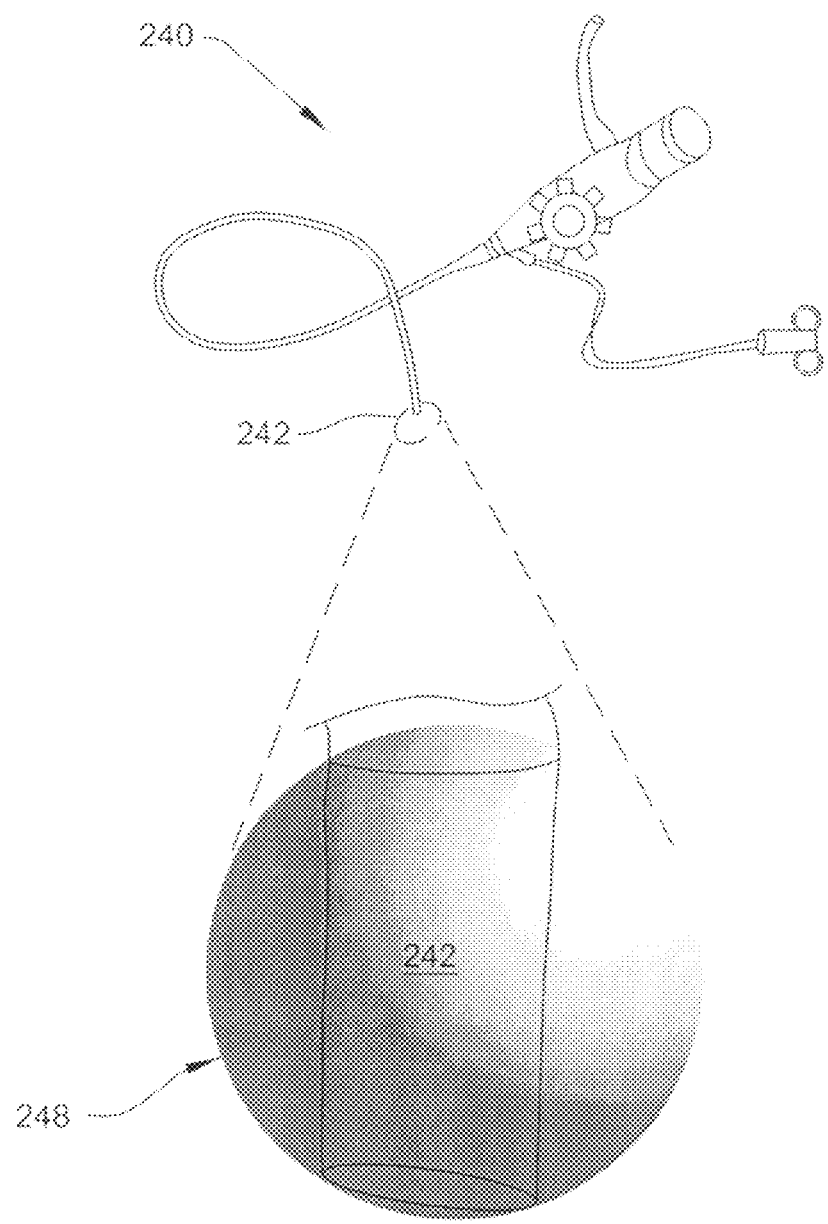
FIG. 10 illustrates the determination of a surgical instrument operating constraint utilizing a bounding sphere.

FIG. 10 illustrates one example of determining an operating constraint of a surgical instrument 240, such as a flexible endoscope. In the present example, the smallest rigid segment of the instrument is identified as being the distal tip section 242 of the instrument 240. A bounding sphere 248 is then defined that is just sufficiently large enough to encompass the distal tip section 242 of the instrument 240.

Scaling of the Volumetric Scan of the Patient Based on the Operating Constraints of a Surgical Instrument According to one embodiment, the navigational system 100 scales the volumetric scan of the patient to account for any operating constraints of the surgical instruments being used during a specific procedure (Step 147). For example, a bounding sphere of a previously calculated size represents a discrete step or smallest unit of displacement that a surgical instrument can take as that instrument is guided through the body of the patient. To account for this limitation of the instrument, the surgical navigation system 100 scales down the CT scan of the patient such that each point or smallest distinguishable unit of the scan (e.g., 3-D voxel) is now equivalent in size to that of the bounding sphere.

During the scaling process, the system 100 must calculate an adjusted weight value W' of each point, now equivalent in size to the bounding sphere, of the newly scaled CT scan. According to one embodiment, the adjusted weight value W' of each scaled point is established as the median of all the weight values W of the original voxels that resided within a volume defined by the size of the previously calculated bounding sphere.

Figure 11:
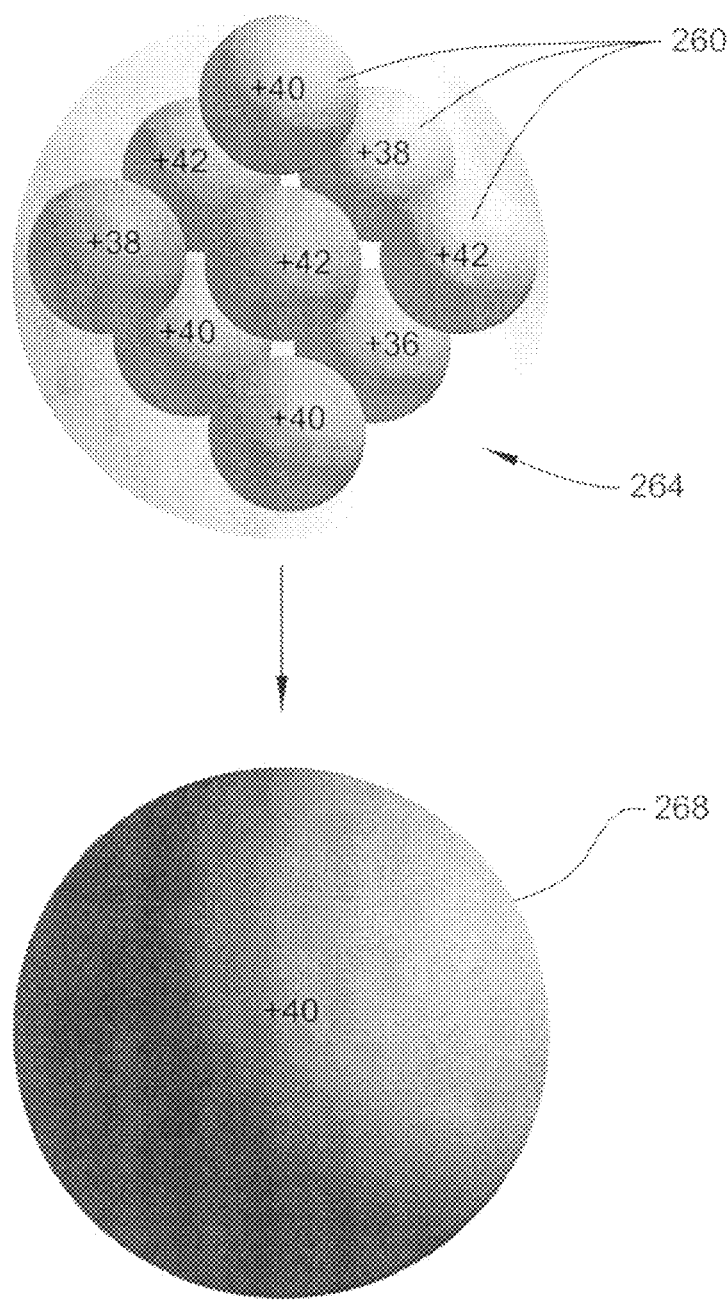
FIG. 11 is an illustrative example of a process for scaling down a volumetric scan of a patient.

FIG. 11 is an illustrative example of the above scaling process, wherein the system 100 effectively reduces the resolution of the original CT scan by reducing the number of voxels that make up the scan. This scaling process, and subsequent reduction in resolution, is accomplished by segregating the original scan into regions that are equivalent in size to the previously calculated bounding sphere. Each such defined region then effectively becomes a new voxel, or smallest distinguishable unit of volume, of the newly scaled down CT scan. The adjusted weight value W' of each of the newly created voxels of the scaled scan is set to be equivalent to the median weight value W of the original voxels that resided within the region defined by the bounding sphere.

To further illustrate the above process, FIG. 11 depicts a collection of voxels 260 that make up the original CT scan, with each such voxel 260 depicted with their assigned weight value W. Original voxels 260 are subsequently segregated into regions 264 that are equivalent in size to a calculated bounding sphere. To effectuate the scaling process, each such region 264 is established as a new voxel 268, now representing the smallest distinguishable unit of volume of the scaled-down CT scan. Furthermore, each new voxel 268 is assigned an adjusted weight value W' that is equivalent to the median of all the weight values W of the original voxels 260 that resided within region 264.

As mentioned above, one consequence of scaling down the original CT scan so as to incorporate the operative constraints of a surgical instrument is that the scaled down CT scan is comprised of fewer voxels, and thus is lower in resolution. This subsequently leads to a significant increase in performance of the navigation system 100 as the scaling procedure reduces the amount of data that the system 100 must process when calculating and later proposing an optimum trajectory or path during the actual surgical procedure.

Modeling a Volumetric Scan of a Patient as a Directed 3-D Graph

The next step in calculating an optimum surgical trajectory is for the system 100 to model a patient's CT scan as a directed three-dimensional graph G comprising a set of vertices V and edges E (Step 148). For example, when the patient's volumetric scan is a three-dimensional CT scan, each vertex V represents a voxel of the scaled down scan, with each voxel having an associated Hounsfield radiodensity value. Each edge E, representing one unit length or step within the scaled down scan, is defined by its two endpoints (v,w) or vertices and is assigned a nonnegative cost c(v,w). If a point v is not adjacent point w, then the cost c(v,w) associated with the edge connecting those two points is defined as being infinity. If point v and point w are adjacent to one another, then the edge E connecting those two points is assigned a cost value c(v,w) that is equal to the radiodensity value of point w and which represents the cost associated with going from point v to point w.

Transformation Into an Adjacency Cost Matrix

The directed three-dimensional graph G, as described above, is then transformed into an adjacency cost matrix C (Step 149). The $(i,j)^{th}$ and $(j,i)^{th}$ entries of cost matrix C are set to be equivalent to the corresponding density value P of vertex i if vertex i and vertex j are adjacent to one another. If vertex i and vertex j are not adjacent to one another, then the entries are defined as being infinity, indicating that no permittable path exists between these two vertices.

Figures 12, 13:
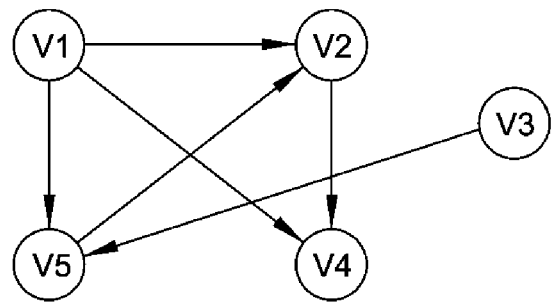
FIG. 12 is an illustrative example of a directed three-dimensional graph G.
FIG. 13 is an illustrative example of an adjacency cost matrix C corresponding to the directed three-dimensional graph G of FIG. 12.

To illustrate the above process, see FIG. 12 and FIG. 13, which depict examples of a directed three-dimensional graph G and corresponding adjacency cost matrix C, respectively. The graph G of FIG. 12 depicts vertices V1 through V5, with arrows indicating those vertices that are connected to one another and having a permittable path between them. Graph G of FIG. 12 is then transformed into corresponding cost matrix C of FIG. 13. Those vertices that have no permittable path between them are indicated as such in the matrix by ∞ (infinity), while those vertices that have permittable paths existing between them are indicated as such in the matrix by the density value P of the destination vertex. Thus, for example, a permittable path exists in traveling from vertex V1 to vertex V4, with the path having an associated cost that is equivalent to the radiodensity value P of vertex V4.

Note that in the above illustrated example of FIGS. 12 and 13, since the graph G has relatively few connections per node, the cost matrix C is modeled as a sparse matrix for memory and performance reasons.

Incorporating Region Preferences into the Cost Matrix

The next step in calculating an optimum surgical trajectory is to modify the cost matrix C, as discussed above, to take into account any restrictions previously specified in any template or programmed maps indicating those anatomical areas that should preferably be utilized or avoided in formulating an optimal surgical path (Step 150). The modified cost matrix C' is calculated as a product of the non-modified cost matrix C and any previously specified maps m (C'=C×m), where maps m associate every point in a patient's volumetric scan with a modified weight value W'. The result of this process is a modified cost matrix C' that incorporates data concerning preferable and undesirable anatomical regions specified a priori.

Modifying the Cost Matrix to Account for Surgical Incisions

The modified cost matrix C' is then further modified so that surgical trajectories or paths requiring fewer incisions in the tissue of the patient are given preferential treatment by system 100 (Step 151). The system 100 presumes that an incision will be required whenever there is a transition from a high radiodensity to a low radiodensity, and vice versa. Modification of the cost matrix C' is accomplished by computing the difference between the adjacent vertices or voxels and then adding the modulus of the difference to the cost matrix C'. The above step effectively increases the cost of, or decreases the preference to use, edges E or steps that require an incision through tissue.

Computation of an Angle Matrix

The system 100 can also take into account curvature analysis in determining an optimal surgical trajectory (Step 152). Each surgical instrument has an associated minimum turning radius indicating the minimum angle at which the instrument can be effectively or safely displaced through tissue. To account for this surgical instrument limitation, system 100 attempts to calculate optimum surgical trajectories that do not require a surgical instrument to be displaced through a curvature that is greater than the rated minimum turning radius of the instrument.

In conducting curvature analysis, system 100 computes an angle matrix A, where A(v,w) is the relative angle made by a line segment joining vertex v to vertex w, which can be considered as a unit vector being directed from vertex v to vertex w. The system 100 can then take the dot product between first and second three-dimensional vectors, with the first vector connecting the first vertex in question (e.g., vertex v) to a third, separate vertex (e.g., vertex Z), and the second vector connecting the second vertex in question (e.g., vertex w) to the third vertex (vertex Z), thereby determining the angle that exists between vertices v and w.

Accounting for Distance in a Surgical Trajectory

In one embodiment, system 100 can also account for distances in a surgical trajectory or path, with preference for trajectories/paths that reach the desired destination in the least distance (Step 153).

To accomplish the above, system 100 modifies cost matrix C' to incorporate distance as a function of cost in calculating an optimum surgical trajectory. Specifically, the system 100 computes a distance matrix D, where D(v,w) is the physical distance that a surgical instrument would need to be displaced when traveling from vertex v and vertex w. The further modified cost matrix C" can be expressed mathematically as $C''=b*D+(1-b)*C'$, where b is the weight.

Computation of the All-Pairs Shortest Path

To determine the shortest, acceptable path between two non-adjacent vertices, the system 100 determines the optimum trajectory or path between two non-adjacent vertices such that the cost or sum of the modified weight values W' of the constituent sections or edges making up the proposed trajectory is minimized (Step 154).

According to one embodiment, this is accomplished by computing the all-pairs shortest path, which in turn consists of finding the shortest distance between every pair of vertices in the directed graph G. More specifically, given a directed graph G, where each edge E(v,w) has an associated cost C(v,w), one must find for every non-adjacent pair of vertices the trajectory or path that connects these two vertices and which provides the lowest cost or lowest total weight value.

One proven algorithm for solving the all-pairs shortest path problem is Floyd's algorithm. However, in the current embodiment, system 100 needs to compute the lowest cost path or optimal surgical trajectory that incorporates a minimum local turning radius, which is not taken into account by Floyd's algorithm. To address this limitation, the present invention according to the current embodiment requires the use of a modified version of Floyd's algorithm, one example of which is depicted in FIG. 14. The modified version of Floyd's algorithm accepts as input the modified cost matrix C"(v,w), where the cost is deemed to be infinity if (v,w) is not in edge E. The resultant output of the modified algorithm includes both a distance matrix D(v,w) and a path matrix P.

Distance matrix D(v,w) reveals the lowest cost path, based on distance, from vertex v to vertex w. Initially D(v,w) is equivalent to cost matrix C"(v,w).

Path matrix P represents the actual path or trajectory, where P(v,w) holds the intermediate vertex k on the least cost path between vertices v and w that led to the cost stored in distance matrix D(v,w).

After N number of iterations by system 100, all possible trajectories or paths between all pairs of vertices has been examined. Consequently, distance matrix D(v,w) contains the cost of the lowest cost trajectory or path from vertex v to vertex w using all vertices if necessary.

Application of the Surgical Trajectory Determination System

One example of a practical application of the surgical trajectory determination system 100, according to one embodiment, will now be described.

According to the example, a user wishes to research a specific surgical procedure. For instance, a surgeon may be preparing for an upcoming surgical procedure involving the use of a flexible endoscope, and would like to analyze the potential trajectory or path that he or she should utilize to displace the endoscope through the patient to the target region. Such analysis can be readily accomplished utilizing the system 100.

To carry out the analysis, a volumetric scan of the patient (e.g., CT scan, PET scan, MRI, etc.) must be obtained and input into the system 100. The surgeon can also input into the system 100 preference information identifying anatomical regions that should preferably be utilized or avoided in determining an optimum surgical trajectory for the procedure in question. The type of surgical instrument that is presumably going to be used for the procedure must also be entered into the system 100 so that the system 100 can account for any instrument operating constraints.

The system 100 then undergoes the various steps previously described to compute a path matrix P and distance matrix D based on the volumetric scan of the patient. According to one embodiment, the path matrix P and distance matrix D are computed entirely anew based on the patient scan and various information input into the system 100. Alternatively, the system 100 can start with default path matrices that can subsequently be modified based on the specific scan of the patient under evaluation.

The surgeon can then simulate the surgical procedure by identifying to the system 100 the starting point where the instrument will be passed into the patient, and the destination point representing the anatomical region that is to be viewed or manipulated by the instrument. In response, the system 100 references the calculated matrices and determines an optimum surgical trajectory for displacement of the instrument from the identified starting point to the destination point.

System 100 subsequently presents the proposed optimum trajectory to the surgeon by means of monitor 140. Specifically, the system 100 displays upon monitor 140 the volumetric scan of the patient. Superimposed upon the scan are one or more graphics identifying the optimum surgical trajectory as proposed by the system 100. According to one example, the superimposed graphics comprise one or more lines that depict the currently proposed optimum surgical trajectory.

Figure 15:
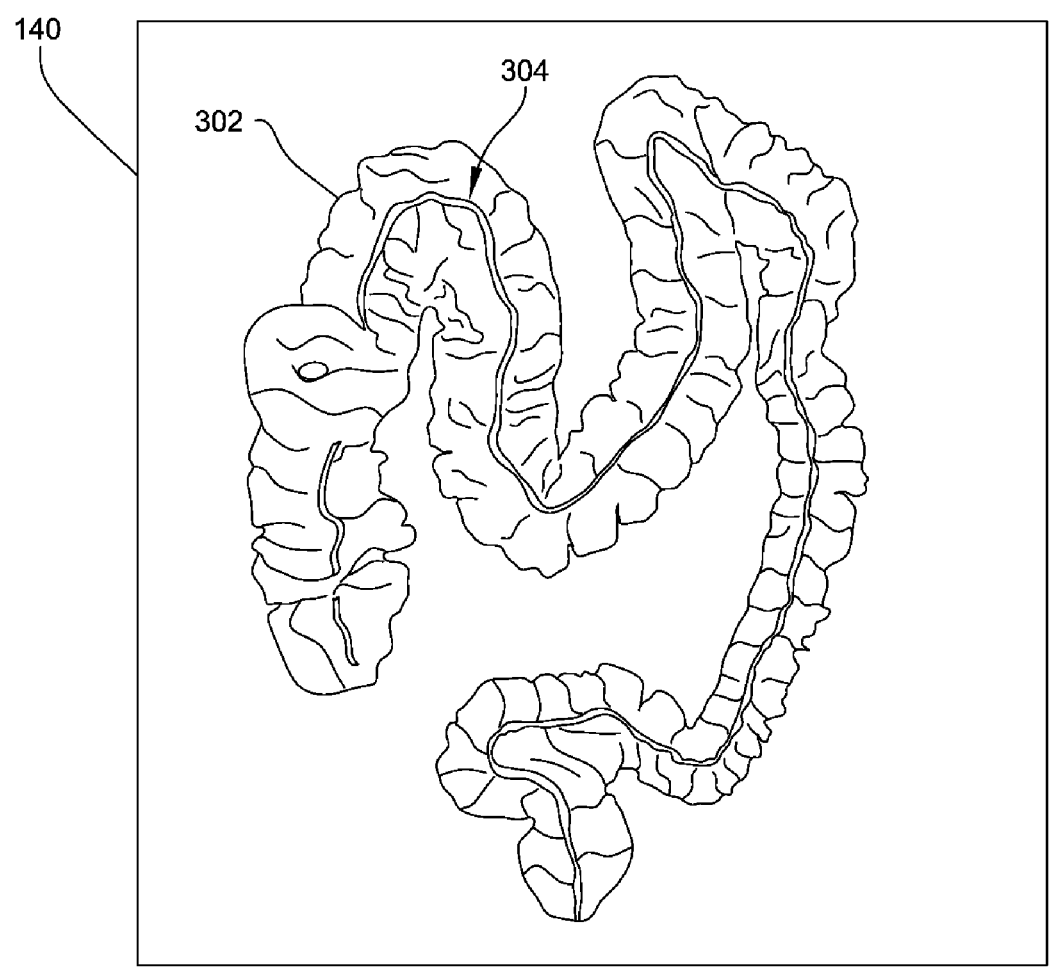
FIG. 15 is an illustrative example of an optimal surgical trajectory being graphically depicted on a volumetric scan of a patient.

For illustrative purposes, and with reference to FIGS. 3 and 15, consider one example where a surgeon is researching the best path or route to take in displacing a surgical instrument through the abdomen of a patient. Based on preference information programmed into the system 100, a first optimal surgical path is proposed that passes through the length of the patient's colon. System 100 subsequently displays on monitor 140 the volumetric scan (e.g., CT scan) of the patient's colon 302. Superimposed upon the image of the colon 302 is a high-lighted line 304 representing the optimal surgical path as determined and proposed by system 100. According to one embodiment, the surgeon can then further analyze the proposed path by manipulating the displayed image of the volumetric scan, including zooming in and out of the scan and rotating the scan in order to visualize the anatomical regions and proposed surgical path from different perspectives.

According to another embodiment, the surgical trajectory determination system 100 can determine and revise a proposed surgical path in essentially real time. Specifically, in evaluating possible surgical trajectories or paths, the surgeon is able to simulate the displacement of the surgical instrument through the patient. Upon detecting such displacement of the virtual surgical instrument, system 100 determines a new optimum surgical path based on the current location of the instrument, and revises in essentially real time the proposed path being graphically depicted on the displayed volumetric scan.

Thus, for example, after being presented with a first proposed optimum surgical trajectory or path on the volumetric scan illustrated on monitor 140, the surgeon begins to simulate displacement of the instrument along the proposed path. At a specific point in time, the surgeon then decides to deviate from the initially proposed surgical path, and simulates displacement of the instrument off of the proposed path and into another region of tissue. System 100 detects the deviation of the instrument from the proposed path, and in response, determines a new optimum surgical path based on the current location of the simulated surgical instrument. The system 100 then revises, in essentially real time, the proposed optimum path being graphically illustrated on the volumetric scan so as to account for the current position of the surgical instrument. Accordingly, system 100 is capable of determining and proposing an optimum surgical trajectory or path for displacing a surgical instrument toward a designated destination, with the proposed optimum path being continuously revised in essentially real time to account for the current position of the instrument.

According to one embodiment, system 100 is configured to continuously determine and revise a proposed optimum surgical trajectory or path upon any detected displacement of the surgical instrument, regardless of whether that displacement follows or deviates from the currently proposed optimum path. Alternatively, the system 100 can be configured to determine and propose a new optimum surgical path only when the system 100 detects that the surgical instrument has been displaced in such a manner so as to deviate from the currently proposed path.

Surgical Navigation System

Figure 16:
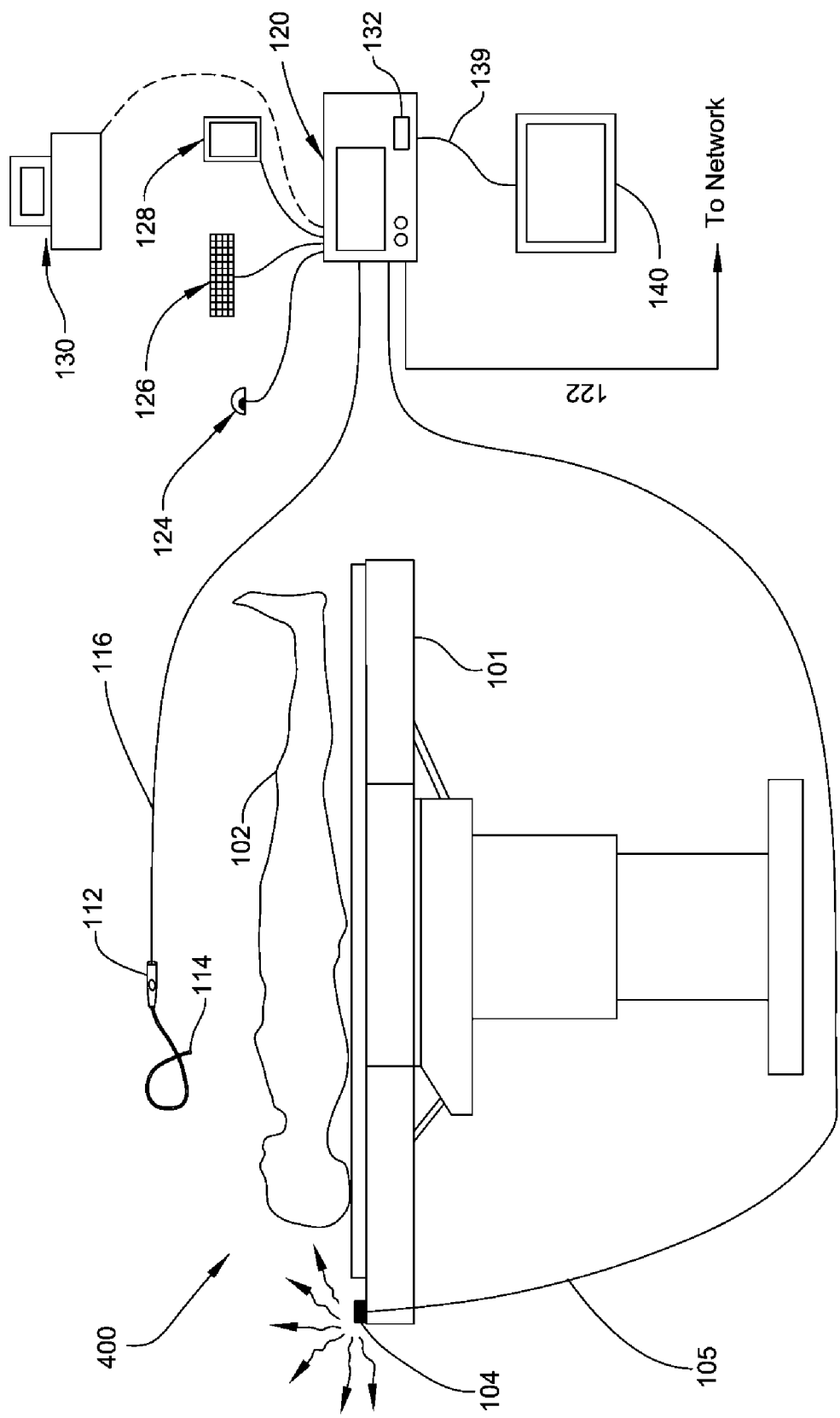
FIG. 16 illustrates a surgical navigation system according to one embodiment of the present invention.

According to another embodiment of the present invention, the methods described above for determining an optimum surgical trajectory are incorporated into a surgical navigation system 400 that can be utilized during the performance of an actual surgical procedure. Specifically, navigation system 400, one example of which is illustrated in FIG. 16, provides information in real-time that assists the surgeon in determining and following an optimal surgical trajectory for an endoscope or other surgical instrument 112 being utilized within the body 102 of a patient lying on a surgical table 101.

Similar to the optimum surgical trajectory determination system 100, navigation system 400 includes a central controller 120, one or more human interface devices 124-128, and at least one monitor 140 or other display device, such as a head mounted display that can be worn by the surgeon. Navigation system 400 can also include one or more separate computers 130 interfacing with central controller 120. For further detail concerning these components, see the previous discussion relating to the optimum surgical trajectory determination system 100.

Navigation system 400 further comprises an electromagnetic tracking and registration system capable of tracking the three-dimensional position and orientation of an actual surgical instrument as the instrument is being utilized within the interior of the patient body 102. The electromagnetic tracking system comprises at least one electromagnetic field (EMF) generator 104 and at least one EMF sensor 114 capable of detecting the wireless electromagnetic signal being transmitted by the EMF generator 104. EMF generator 104 mounts upon the surgical table 101 or is maintained in some other fixed position within the operating room relative to the patient 102, and communicates with the central controller 120 by means of a hard-wired connection 105, or alternatively, a wireless connection (not illustrated).

Also included in the system 400 are one or more surgical instruments 112 for visualizing and/or manipulating the tissue of a patient. Incorporated within or mounted upon at least a distal tip of the surgical instrument 112 is the at least one EMF sensor 114, which communicates with the central controller 120 via an associated wire connection 116 or wireless connection (not illustrated). The one or more EMF sensors 114 receive the wireless signal being transmitted by the EMF generator 104 and convert the received wireless signal into an electrical signal that is subsequently forwarded on to the central controller 120 via communication link 116.

The central controller 120 processes the electrical signal received from the EMF sensor(s) 114 on a near-continuous basis, and is able to determine at any point in time the relative position and orientation of the EMF sensor 114, and thus the relative position and orientation of the surgical instrument 112 itself, relative to the EMF generator 104 and patient body 102. Additional detail concerning operation of the EMF generator(s) 104 and EMF sensor(s) 114, which make up the electromagnetic tracking system, is not being provided in the current application, but can be found in pending U.S. patent application Ser. No. 11/388,756, the disclosure of which is hereby incorporated by reference.

Application of the Surgical Navigation System

One example of a practical application of a surgical navigation system 400 according to one embodiment will now be described with respect to a typical surgical procedure.

In a manner similar to the optimum path determination system 100, a path matrix P and distance matrix D are pre-computed based on the patient's volumetric scan (e.g., CT scan, PET scan, MRI, etc.). According to one embodiment, this process is accomplished by starting with default matrices which are subsequently modified based on the specific patient's scan. Alternatively, entirely new matrices can be developed.

During preparation of the patient's surgery, the path matrix P and distance matrix D, along with the patient's volumetric scan, are loaded into the system 400 by means of central controller 120.

During this preparation period, the spatial position and orientation of the surgical instrument, which is being tracked by the electromagnetic tracking system, is correlated with the co-ordinate system of the patient scan. Correlation of the electromagnetic tracking system to the patient scan can be accomplished in numerous ways, including, for example, by identifying one or more physical points on the patient's body, and then identifying the corresponding point(s) in the patient's volumetric scan. Utilizing these reference points, the system 400 can then register each actual spatial position, as identified by the electromagnetic tracking system, with a position in the volumetric scan. Consequently, the navigation system 400 is able to correlate the position and orientation readings from the one or more EMF sensors 114 to the vertices (e.g., voxels) in the patient's scan.

A user then designates within the patient's scan the position and visiting sequence of the target areas for the upcoming surgical procedure. For example, the surgeon may identify on the scan several anatomical regions (e.g., the appendix, ascending colon, and sigmoid colon) that he or she wishes to examine in sequence.

The surgical procedure is then initiated, and when the surgeon inserts and displaces the surgical instrument 112 within the body 102 of the patient, the system graphically depicts the location of the instrument 112 on the patient's scan being displayed on the monitor 140. With each detected displacement of the instrument 112, the system determines and proposes, in real time, the optimum surgical trajectory or lowest cost path for reaching the next designated target position from the current position of the instrument 112. Since all-pairs shortest path is precompiled, determination of the most optimum path simply involves the system indexing a matrix.

To help guide displacement of the instrument 112 by the surgeon, the system 400 renders, in real time, various graphics depicting the proposed optimum trajectory or path to the target position. The optimum trajectory can be rendered in three-dimensions if a three-dimensional patient scan is being utilized by the system. Alternatively, the optimum trajectory can be rendered on any two-dimensional scans or two-dimensional slices of a three-dimensional scan.

The surgeon can decide to follow the trajectory presented by the system 400, or he or she can choose to deviate from the proposed trajectory. In a manner similar to a vehicle navigation system, if the surgeon deviates from the proposed trajectory, the system 400 will determine and propose a new optimum trajectory for reaching the target position from the current location of the instrument 112. Specifically, as the surgeon displaces the instrument 112 within the body 102 of the patient, the system 400 will continuously determine the position and orientation of the instrument 112 and, in real time, update and propose the most optimum trajectory to reach the designated target from the current location of the instrument 112.

In the above manner, the surgeon is seen to always be in control of the optimum trajectory or path proposed by the system 400. If the surgeon disagrees with the proposed trajectory, he or she is free to deviate from it, thereby prompting the system 400 to automatically determine and propose a new optimum path based upon the actions of the surgeon. Accordingly, the surgeon is able to combine his experience and knowledge with the computational power and intelligence of the system, thereby allowing the surgeon to safely and efficiently navigate within the body of the patient.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. An interactive method of determining an optimum surgical trajectory for displacing a flexible surgical instrument through the interior of a body of a patient, comprising the steps of:
   assigning weight values to one or more regions identified in a volumetric scan of a patient, the weight values indicating a degree of preference that a specified region be utilized to receive the flexible surgical instrument in calculating the optimum surgical trajectory;
   calculating the optimum surgical trajectory between every two non-adjacent regions identified in the volumetric scan of the patient;
   presenting the optimum surgical trajectory to a user on a display in response to identification of a starting region and a destination region within the volumetric scan of the patient;
   steering a distal end of the flexible surgical instrument in the interior of the body of a patient; and
   revising the optimum surgical trajectory presented on the display, essentially in real time, in response to an indicated current position of the flexible surgical instrument changing as a result of user interaction.

2. The method according to claim 1, further comprising the step of preparing one or more matrices of values representing the optimum surgical trajectory between every two non-adjacent regions within the volumetric scan of the patient; and
   wherein the step of revising the optimum surgical trajectory presented to the user on the display in response to the indicated current position of the flexible surgical instrument includes referencing the indicated current position relative to the one or more prepared matrices.

3. The method according to claim 1, wherein the step of assigning weight values comprises application of a predetermined template containing a map indicating one or more regions and the assigned weight values for the regions.

4. The method according to claim 1, wherein the step of assigning weight values comprises the steps of manually identifying regions on the scan, and manually assigning a weight value to each identified region.

5. The method according to claim 1, further comprising the step of accounting for one or more operative constraints of the flexible surgical instrument in calculating the optimum surgical trajectory.

6. The method according to claim 5, further comprising the step of determining a minimum size of a bounding sphere that can encompass a region of the surgical instrument associated with the operative constraint from a smallest rigid segment disposed at the distal end of the flexible surgical instrument and its center of rotation.

7. The method according to claim 1, wherein the regions represent one of a smallest distinguishable unit of area and a smallest distinguishable unit of volume in the volumetric scan.

8. The method according to claim 7, further comprising the step of quantifying the regions of the volumetric scan with property values representing a measurable property of a tissue represented by each region, wherein the measurable property of the tissue comprises one of a radiodensity of tissue, an electromagnetic response of tissue to an emittance of radiotracers introduced into the tissue, a magnetic resonance of tissue, and acoustic reflectivity of tissue.

9. The method according to claim 1, further comprising the step of scaling the volumetric scan so as to be comprised of regions corresponding in size to that of a bounding sphere associated with an operative constraint of the instrument.

10. The method according to claim 1, further comprising the steps of determining whether displacement of the flexible surgical instrument will require an incision in the tissue of the patient, and determining an optimum surgical trajectory that requires the least number of tissue incisions.

11. The method according to claim 1, further comprising the step of accounting for physical distance between regions in the volumetric scan, and determining the optimum surgical trajectory between two identified regions that accounts for the assigned weight values while minimizing the physical distance of the trajectory.

12. The method according to claim 1, further comprising the steps of:
   determining a minimum turning radius of the flexible surgical instrument; and
   applying curvature analysis in the calculating of an optimum surgical trajectory so as to prefer optimum surgical trajectories that do not require the flexible surgical instrument to be displaced through a curvature that exceeds the determined minimum turning radius of the surgical instrument.

13. The method according to claim 1, further comprising the step of automatically detecting the current position of the flexible surgical instrument utilizing an electromagnetic tracking system configured to track the three-dimensional position and orientation of the flexible surgical instrument relative to the patient body.

14. The method according to claim 13, further comprising the step of correlating regions of the patient's body to regions within the volumetric scan of the patient, thereby allowing the electromagnetic tracking system to track the three-dimensional position and orientation of the flexible surgical instrument relative to the volumetric scan of the patient.

15. The interactive method according to claim 1, including the steps of:
  displaying a proposed optimum surgical trajectory and the volumetric scan on the display; and
  evaluating possible proposed surgical trajectories by the surgeon simulating the displacement of the flexible surgical instrument within the patient to determine the optimum surgical trajectory based on preference information programmed into the system or according to preferences of the surgeon,
  wherein the step of presenting the optimum surgical trajectory to a user comprises presenting the optimum surgical trajectory determined by the evaluating of the possible proposed surgical trajectories.

16. The method according to claim 1, wherein the step of revising the optimum surgical trajectory comprises continuously revising the optimum surgical trajectory regardless of whether the displacement of the flexible surgical instrument follows or deviates from the optimum surgical trajectory as a result of user interaction.

17. The method according to claim 1, wherein the step of revising the optimum surgical trajectory comprises revising the optimum surgical trajectory only when the indicated current position of the flexible surgical instrument deviates from the optimum surgical trajectory as a result of user interaction.

18. The method according to claim 1, wherein the step of steering the flexible surgical instrument comprises manual steering of the flexible surgical instrument by the surgeon to displace the instrument along the optimum surgical trajectory.

19. The method according to claim 1, wherein the flexible surgical instrument comprises a semi-rigid or flexible endoscope.

20. A method of aiding a surgeon in guiding a flexible surgical instrument through the body of a patient, comprising the steps of:
  obtaining a volumetric scan of the body;
  determining an initial optimum path for displacing the flexible surgical instrument from its current position to a designated destination position within the body based on data derived from the volumetric scan;
  presenting the initial optimum path to the surgeon during a surgical procedure;
  steering a distal end of the flexible surgical instrument to displace the instrument along the optimum path in the interior of the body of a patient;
  determining in essentially real time a new optimum path for displacing the flexible surgical instrument from its current position within the body to the designated destination position within the body when displacement of the flexible surgical instrument has been detected; and
  presenting the new optimum path to the surgeon in essentially real time during the surgical procedure.

21. The method according to claim 20, wherein the step of determining a new optimum path for displacing the flexible surgical instrument occurs in essentially real time only when displacement of the flexible surgical instrument deviates from the initially determined optimum path is detected.

22. The method according to claim 20, further comprising the steps of determining whether displacement of the flexible surgical instrument will require an incision in the tissue, and determining an optimum path that requires the least number of tissue incisions.

23. The method according to claim 20, wherein the volumetric scan comprises one of an x-ray scan, computed tomography (CT) scan, magnetic resonance imaging (MRI) scan, positron emission tomography (PET) scan, and ultrasound scan.

24. The method according to claim 20, wherein the scan is comprised of a plurality of regions that represent one of a smallest distinguishable unit of area in the scan, and a smallest distinguishable unit of volume in the scan.

25. The method according to claim 24, further comprising the step of quantifying the regions of the scan with property values representing a measurable property of a tissue represented by each region, wherein the measurable property of the tissue comprises one of a radiodensity of tissue, an electromagnetic response of tissue to an emittance of radiotracers introduced into the tissue, a magnetic resonance of tissue, and acoustic reflectivity of tissue.

26. The method according to claim 24, further comprising the step of assigning weight values to each region of the scan, the weight values representing the surgeon's degree of preference that an anatomical area either be avoided or passed through during displacement of the surgical instrument toward the designated destination position.

27. The method according to claim 26, wherein the weight values of each region are determined based on a measurable property of a tissue represented by each region.

28. The method according to claim 26, wherein the step of assigning weight values comprises application of a predetermined template containing a map indicating one or more anatomical areas and the assigned weight values.

29. The method according to claim 26, wherein the step of assigning weight values comprises the steps of manually identifying anatomical areas on the scan, and manually assigning a weight value to each identified anatomical area.

30. The method according to claim 20, further comprising the step of determining an operative constraint of the flexible surgical instrument.

31. The method according to claim 30, further comprising the steps of determining a minimum size bounding sphere that can encompass a region of the flexible surgical instrument associated with the operative constraint, and scaling the volumetric scan so as to be comprised of regions corresponding in size to that of the bounding sphere.

32. The method according to claim 20, further comprising the step of displaying at least one of graphics or text identifying the optimum path on a display of an image captured by the flexible surgical instrument.

33. The method according to claim 32, wherein the graphics or text comprise prompts to the surgeon indicating a direction in which the flexible surgical instrument should be displaced to maintain the optimum path.

34. The method according to claim 20, wherein the step of steering comprises manual steering by the surgeon, and the step of presenting the new optimum path to the surgeon in essentially real time during the surgical procedure occurs upon the displacement of the distal end of the flexible surgical instrument.

35. The method according to claim 20, wherein the step of determining in essentially real time the new optimum path comprises continuously determining in essentially real time the new optimum path regardless of whether the displacement of the flexible surgical instrument follows or deviates from the optimum path.

36. The method according to claim 20, wherein the flexible surgical instrument comprises a semi-rigid or flexible endoscope.

37. A method of aiding a surgeon in guiding a flexible surgical instrument through the body of a patient, comprising the steps of:
obtaining a multi-dimensional scan of the body comprising a plurality of definable positions;
determining whether displacement of the surgical instrument will require an incision in the tissue;
determining an optimum path that requires the least number of tissue incisions;
calculating a trajectory for displacing the flexible surgical instrument between any position in the scan to any other position in the scan, with each trajectory representing an optimum path for displacing the flexible surgical instrument from one position within the body to another position within the body;
determining a current position of the flexible surgical instrument during a surgical procedure;
presenting to the surgeon in real time the optimum path for displacing the flexible surgical instrument from its currently detected position to a designated destination position;
steering a distal end of the flexible surgical instrument in the interior of the body of a patient; and
revising in real time the optimum path presented to the surgeon in response to displacement of the flexible surgical instrument.

38. The method according to claim 37, wherein the scan of the body is a two-dimensional scan, with each said definable position comprising the scan representing a smallest distinguishable unit of area within the scan.

39. The method according to claim 37, wherein the scan of the body is a three-dimensional scan, with each said definable position comprising the scan representing a smallest distinguishable unit of volume within the scan.

40. The method according to claim 37, wherein each position in the scan can be quantified with a property value representing a measurable property of a tissue in the body corresponding to that position in the scan, and wherein the step of determining whether displacement of the flexible surgical instrument will require an incision is based on whether the displacement of the flexible surgical instrument is between two positions of the scan having dissimilar property values.

41. The method according to claim 37, further comprising the step of assigning weight values to each position in the scan, the weight values representing a degree of preference that an anatomical area either be avoided or passed through during displacement of the flexible surgical instrument toward the designated destination position.

42. The method according to claim 41, wherein the step of assigning weight values comprises application of at least one predetermined template containing a map indicating one or more positions and their assigned weight values.

43. The method according to claim 41, wherein the step of assigning weight values comprises the steps of manually identifying regions on the scan comprised of a plurality of positions, and manually assigning a weight value to each identified region.

44. The method according to claim 37, further comprising the step of accounting for one or more operative constraints of the flexible surgical instrument in calculating the optimum path for displacing the surgical instrument.

45. The method according to claim 44, wherein the flexible surgical instrument comprises a semi-rigid or flexible endoscope, and further comprising the step of determining a minimum size bounding sphere that encompasses a region of the semi-rigid or flexible endoscope associated with the operative constraint.

46. The method according to claim 45, further comprising the step of scaling the multi-dimensional scan by adjusting the smallest distinguishable region within the scan, represented by the plurality of positions comprising the scan, to correlate in size to the determined minimum size bounding sphere.

47. The method according to claim 37, further comprising the step of displaying at least one of graphics or text on one or more displays depicting an image captured by the flexible surgical instrument.

48. The method according to claim 47, wherein the graphics or text comprise prompts to the surgeon indicating a direction in which the flexible surgical instrument should be displaced to maintain the optimum path.

49. The method according to claim 37, wherein the step of steering the flexible surgical instrument comprises manual steering of the flexible surgical instrument by the surgeon to displace the instrument along the optimum path.

50. The method according to claim 37, wherein the step of revising in real time the optimum path comprises revising the optimum path only when the flexible surgical instrument deviates from the optimum path in response to the displacement of the flexible surgical instrument.

51. A system for aiding a surgeon in guiding a semi-rigid or flexible endoscope through the body of a patient, comprising:
a central controller for receiving a volumetric scan of the patient and producing a map of anatomical areas of the patient quantified with property values representing a measurable property of tissue comprising the anatomical areas;
at least one data input interface on the central controller for receiving data representing weight values associated with the anatomical areas of the patient, the weight values representing a degree of preference that an anatomical area either be avoided or passed through during displacement of the endoscope toward a designated destination;
an electromagnetic tracking system for determining the three-dimensional position and orientation of the endoscope as the endoscope is displaced through the interior of the patient body; and
at least one monitor for displaying at least one of the volumetric scan of the patient and an image captured by the endoscope,
wherein the central controller is configured to determine an optimum surgical path for displacing the endoscope from a first location within the patient to the designated destination within the patient, the optimum path being determined based on the map of anatomical areas of the patient and the data representing weight values associated with the anatomical areas of the patient, and
wherein the central controller is configured to update and present to the surgeon in real time, upon detected displacement of the endoscope, an updated optimum surgical path for displacing the endoscope from its current location to the designated destination, and
wherein the central controller is configured to receive information concerning a center of rotation for steering of the endoscope that is utilized to determine any operative constraints associated with the endoscope.

* * * * *